United States Patent
McKnight et al.

(10) Patent No.: US 9,609,862 B2
(45) Date of Patent: Apr. 4, 2017

(54) CHOLINE CHLORIDE IN LIQUID GUAR FORMULATIONS

(71) Applicant: RHODIA OPERATIONS, Paris (FR)

(72) Inventors: Michelle McKnight, Philadelphia, PA (US); Leahann Iannotta, Wayne, PA (US); Thomas Ruch, Voorhees, NJ (US)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 14/792,750

(22) Filed: Jul. 7, 2015

(65) Prior Publication Data

US 2016/0000070 A1 Jan. 7, 2016

Related U.S. Application Data

(60) Provisional application No. 62/021,262, filed on Jul. 7, 2014.

(51) Int. Cl.

| | | |
|---|---|---|
| *A01N 25/04* | (2006.01) | |
| *A01N 25/30* | (2006.01) | |
| *B65H 54/44* | (2006.01) | |
| *B65H 54/553* | (2006.01) | |
| *B65H 57/16* | (2006.01) | |
| *C09K 8/03* | (2006.01) | |

(52) U.S. Cl.
CPC ............ *A01N 25/04* (2013.01); *A01N 25/30* (2013.01); *C09K 8/03* (2013.01)

(58) Field of Classification Search
None
See application file for complete search history.

(56) References Cited

U.S. PATENT DOCUMENTS

| | | |
|---|---|---|
| 5,268,466 A | 12/1993 | Burdick |
| 6,288,010 B1 | 9/2001 | Rose et al. |
| 9,441,150 B2 * | 9/2016 | Lord ............... C09K 8/512 |
| 2002/0019318 A1 | 2/2002 | Harris |
| 2006/0073982 A1 | 4/2006 | Patel et al. |
| 2008/0181922 A1 | 7/2008 | Steckler et al. |
| 2011/0054042 A1 | 3/2011 | Wu et al. |
| 2012/0122688 A1 | 5/2012 | Wu et al. |
| 2014/0066303 A1 | 3/2014 | Liu et al. |

FOREIGN PATENT DOCUMENTS

| | | |
|---|---|---|
| CN | 102823591 A | 12/2012 |
| CN | 103348975 A | 10/2013 |
| CN | 103583518 A | 2/2014 |
| EP | 0448538 A1 | 9/1991 |
| EP | 2505061 A1 | 10/2012 |
| FR | 2873593 A1 | 2/2006 |
| WO | 2012113830 A2 | 8/2012 |

\* cited by examiner

*Primary Examiner* — Ernst V Arnold

(57) ABSTRACT

A concentrated adjuvant composition comprises an incompletely hydrated water-soluble polymer suspended in a liquid medium, a suspension agent and a hydration inhibitor component.

23 Claims, No Drawings

CHOLINE CHLORIDE IN LIQUID GUAR FORMULATIONS

CROSS-REFERENCE TO RELATED APPLICATIONS

This application claims the benefit of U.S. Provisional Patent Application No. 62/021,262 filed Jul. 7, 2014, incorporated herein by reference in its entirety.

FIELD OF THE INVENTION

This invention relates to formulations having concentrated suspensions of water-soluble polymers and, in particular, to concentrated suspensions of polysaccharide particles.

BACKGROUND

Water-soluble polymers, particularly polysaccharide polymers, such as, for example, guar, guar derivatives, starches, and cellulosic polymers, are commercially available materials used in a variety of applications, including as ingredients in food products, personal care compositions, agricultural pesticide compositions, and compositions, such as fracturing fluids, for use in oilfield applications.

SUMMARY OF THE INVENTION

In many agricultural applications, a polymer in the form of a dry powder is added to an aqueous medium and dissolved to form a viscous aqueous solution. In some applications, it would also be desirable to provide a liquid concentrate that has a high polymer content and that could simply be diluted to the desired end-use concentration for agricultural uses. This approach can be difficult, for example, concentrated aqueous polysaccharide polymer solutions tend to be highly viscous and difficult to handle. Often times, ammonium containing compounds such as ammonium sulphate (AMS), diammonium phosphate (DAP), and urea ammonium nitrate (UAN) can be used to control polysaccharide hydration.

In the agricultural industry, ammonium containing compounds such as ammonium sulphate (AMS), diammonium phosphate (DAP), and urea ammonium nitrate (UAN), among others, are conventionally used to control polysaccharide hydration as well as in water conditioning. Use of AMS, DAP and UAN, among others, have been widely adopted in agricultural practices, especially in "hard water" areas. In these areas, tank mixes containing, as a large component thereof, "hard water" along with pesticides, including herbicides (e.g., glyphosate) and the like, as well as other components.

To combat the rise of glyphosate-resistant weeds, the trend in the agricultural industry has shifted away from utilizing only glyphosate to other herbicides or a combination of glyphosate with other herbicides. Other herbicides, for example, dicamba and its salts, can be utilized. However, dicamba and its salts are generally incompatible with ammonium containing compounds used for water conditioning. As such, it is desirable to replace these ammonium containing compounds with alternative compounds that are compatible with dicamba and its salts. In one embodiment, the compositions as described herein are free of added ammonium containing compounds or are prepared in the absence of ammonium containing compounds. In another embodiment, the composition as described herein are substantially free of ammonium containing compounds, meaning no ammonium containing compounds have been added to the composition.

There is also a continuing interest in providing polymers in a convenient form that exhibits good handling properties and good storage stability.

In a first aspect, described herein are concentrated adjuvant compositions, comprising, based on 100 parts by weight of the composition:—greater than 1 parts by weight (otherwise referred to herein as "pbw") of an incompletely hydrated water-soluble polymer suspended in a liquid medium;—a hydration inhibitor component; and—a suspending agent in an amount effective to impart shear thinning properties to the composition. The water-soluble polymer is, in some embodiments, a water-soluble polysaccharide polymer. In one embodiment, the hydration inhibitor component comprises choline chloride. In another embodiment, the hydration inhibitor component comprises potassium phosphate (dibasic). It is understood that potassium phosphate (dibasic) is also referred to as dipotassium phosphate ($K_2HPO_4$). In yet another embodiment, the hydration inhibitor component comprises a combination of choline chloride and potassium phosphate (dibasic).

In a another aspect, described herein are concentrated adjuvant compositions, comprising, based on 100 parts by weight of the composition:—greater than 1 parts by weight of an incompletely hydrated water-soluble polymer suspended in a liquid medium;—a hydration inhibitor component; and—a suspending agent in an amount effective to impart shear thinning properties to the composition, wherein the concentrated adjuvant composition is substantially free of ammonium containing compounds. In another embodiment, the concentrated adjuvant composition is free of added ammonium containing compounds.

In one embodiment, the concentrated adjuvant composition can comprise one or more surfactants, glycerine, a water conditioning agent or a mixture thereof. In one embodiment, the suspending agent is selected from fumed silica, inorganic colloidal or colloid-forming particles, rheology modifier polymers, or mixtures thereof.

The hydration inhibitor component is typically present in an amount effective to inhibit hydration of the water-soluble polysaccharide in the desired amount in the aqueous medium.

In another embodiment, the hydration inhibitor component can further comprise at least one of: one or more surfactant compounds, one or more water-soluble non-surfactant salts, or one or more water dispersible organic solvents.

In another embodiment, the concentrated adjuvant composition can further comprise a pesticide active ingredient, wherein the water-soluble polymer enhances delivery of the pesticide active ingredient from the liquid medium to a target substrate.

The liquid medium can be an aqueous liquid medium, in one embodiment. In another embodiment, the liquid medium is water. In another embodiment, the liquid medium is water and a water miscible organic liquid.

In yet another embodiment, the liquid medium is an aqueous liquid medium that comprises water and a water immiscible organic liquid. The resulting composition can be in the form of an emulsion, a microemulsion, or a suspoemulsion.

In one embodiment, the water-soluble polymer is selected from polyacrylamide polymers, non-derivatized guar polymers, derivatized guar polymers, and mixtures thereof, and—the suspending agent is selected from fumed silicas, inorganic colloidal or colloid-forming particles, rheology modifier polymers, water-soluble polysaccharide polymers other than the non-derivatized or derivatized guar polymer, and mixtures thereof.

In one embodiment, the concentrated adjuvant composition exhibits a viscosity of less than 10 Pa·s at a shear rate of greater than or equal to 10 s$^{-1}$.

In another aspect, described herein are concentrated adjuvant compositions, comprising, based on 100 parts by weight of the composition,—from about 2 to about 20 parts by weight of a guar polymer suspended in aqueous medium, said guar polymer having a weight average molecular weight of from about 100,000 to about 5,000,000 grams per mole;
    a hydration inhibitor component; and
    a suspending agent in an amount effective to impart shear thinning properties to the composition;
    wherein said composition exhibits:
        (a) a viscosity of greater than or equal to 5 Pa·s at a shear rate of less than 0.01 s$^{-1}$, and
        (b) a viscosity of less than 5 Pa·s at a shear rate of greater than 10 s$^{-1}$.

In one embodiment, the hydration inhibitor component comprises choline chloride. In another embodiment, the hydration inhibitor component comprises potassium phosphate (dibasic). In yet another embodiment, the hydration inhibitor component comprises a combination of choline chloride and potassium phosphate (dibasic). In another embodiment, the hydration inhibitor component comprises choline chloride, choline bicarbonate, choline dihydrogen citrate, choline bitarate, potassium hydrogen phosphate, potassium carbonate, potassium phosphate (dibasic), or any combination thereof. In another embodiment, the hydration inhibitor component comprises a choline salt, choline chloride, choline bicarbonate, choline dihydrogen citrate, choline bitarate, potassium hydrogen phosphate, potassium carbonate, potassium phosphate (dibasic), or any combination thereof.

In another embodiment, the guar polymer comprises from about 2.5 parts to about 12 parts by weight based on 100 parts by weight of the composition. In yet another embodiment, the guar polymer comprises from about 2.5 parts to about 9 parts by weight based on 100 parts by weight of the composition. In another embodiment, the guar polymer comprises from about 1 part to about 20 parts by weight based on 100 parts by weight of the composition. In another embodiment, the guar polymer comprises from about 3 parts to about 6 parts by weight based on 100 parts by weight of the composition. In another embodiment, the guar polymer comprises from about 2 parts to about 12 parts by weight based on 100 parts by weight of the composition.

In another aspect, disclosed herein are methods for making a concentrated adjuvant composition that comprises a mixture of an aqueous liquid medium, an incompletely hydrated water-soluble polymer dispersed in the aqueous liquid medium, and a hydration inhibitor component for inhibiting hydration of the water-soluble polymer, the steps comprising:
    contacting the hydration inhibitor component with the aqueous liquid medium, and
    contacting the water-soluble polymer with the mixture of aqueous liquid and hydration inhibitor component to disperse the water-soluble polymer,
    wherein the hydration inhibitor component comprises, in some embodiment, choline chloride, potassium phosphate (dibasic) or a combination thereof or, in other embodiment, the hydration inhibitor component comprises choline chloride, choline bicarbonate, choline dihydrogen citrate, choline bitarate, potassium hydrogen phosphate, potassium carbonate, potassium phosphate (dibasic), or any combination thereof.

In a further aspect, described herein are methods for making an agricultural pesticide composition, comprising mixing the composition as described herein with an agricultural pesticide compound, optionally other agricultural adjuvants, and water to form an pesticide composition for spray application to target pests. In one embodiment, the composition is free or substantially free of ammonium-containing compounds.

DETAILED DESCRIPTION OF INVENTION AND PREFERRED EMBODIMENTS

As used herein, "liquid medium" means a medium that is in the liquid phase at a temperature of 25° C. and a pressure of one atmosphere. The liquid medium may be a non-aqueous liquid medium or an aqueous liquid medium.

In one embodiment, the liquid medium is an aqueous liquid medium. As used herein, the terminology "aqueous medium" means a single phase liquid medium that contains more than a trace amount of water, typically, based on 100 pbw of the aqueous medium, more than 0.1 pbw water. Suitable aqueous media more typically comprise, based on 100 pbw of the aqueous medium, greater than about 5 pbw water, even more typically greater than 10 pbw water. In one embodiment, the aqueous emulsion comprises, based on 100 pbw of the aqueous medium, greater than 40 pbw water, more typically, greater than 50 pbw water. The aqueous medium may, optionally, further comprise water-soluble or water miscible components dissolved in the aqueous medium. The terminology "water miscible" as used herein means miscible in all proportions with water. Suitable water miscible organic liquids include, for example, ($C_1$-$C_6$) alcohols, such as methanol, ethanol, propanol, and ($C_1$-$C_6$) polyols, such as glycerol, ethylene glycol, propylene glycol, and diethylene glycol, The composition of the present invention may, optionally, further comprise one or more water insoluble or water immiscible components, such as a water immiscible organic liquid, wherein the combined aqueous medium and water insoluble or water immiscible components form a micro emulsion, or a multi-phase system such as, for example, an emulsion, a suspension or a suspoemulsion, in which the aqueous medium is in the form of a discontinuous phase dispersed in a continuous phase of the water insoluble or water immiscible component, or, more typically, the water insoluble or water immiscible component is in the form of a discontinuous phase dispersed in a continuous phase of the aqueous medium.

As used herein, the term "hydration" in reference to the water-soluble polymer component of the present invention means association of substituent groups, typically hydrophilic substitutent groups, such as hydroxyl groups, of the water-soluble polymer with water molecules, such as water molecules of the aqueous medium through, for example, hydrogen bonding. The degree to which the water-soluble polymer is hydrated can range from non-hydrated to completely hydrated, with degrees of partial hydration extending between the two extremes. As discussed more fully below, the water-soluble polymer is capable of contributing to the viscosity of the composition of the present invention with the magnitude of the contribution being dependent on the degree of hydration of the water-soluble polymer. The degree of hydration of the water-soluble polymer can thus be characterized based on the magnitude of the contribution that the water-soluble polymer makes to the viscosity of the composition.

As referred to herein a "non-hydrated" water-soluble polymer makes no significant contribution to the viscosity of the composition. In general, the non-hydrated water-soluble polymer would be in the form of a discontinuous phase, for example, discrete particles, that is dispersed in a continuous phase of the liquid medium, ideally with no interaction between the hydrophilic substituents of the polymer and any water molecules present in the liquid medium. In the case of an aqueous medium, there will generally be at least some interaction between the hydrophilic groups of polymer and water molecules of the aqueous medium at interfaces between the phases, for example, at the outer surfaces of the particles. It is believed that in the case of a non-hydrated water-soluble polymer, interaction among the hydrophilic substituent groups of the non-hydrated water-soluble polymer dominates over interaction between the hydrophilic substituent groups of the polymer and any water molecules present in the aqueous medium, the polymer chains of the non-hydrated water-soluble polymer are in a compact, folded conformation, and, in the case where the liquid medium is an aqueous medium, the non-hydrated water-soluble polymer is not dissolved in the aqueous medium and remains in the form of a discontinuous phase dispersed in the continuous phase of the aqueous medium.

As referred to herein, a "completely hydrated" water-soluble polymer makes the maximum contribution to the viscosity of the composition that the water-soluble polymer is capable of making. It is believed that in a completely hydrated water-soluble polymer, association between the hydrophilic substituent groups of the water-soluble polymer and water molecules dominates over interaction among the hydrophilic substituent groups, that the polymer chains of a completely hydrated water-soluble polymer are thus in an unfolded, random coil conformation, and in the case where the liquid medium is an aqueous medium, the aqueous medium and completely hydrated water-soluble polymer form a single phase, that is, the completely hydrated water-soluble polymer is dissolved in the aqueous medium.

As referred to herein, a "partially hydrated" water-soluble polymer is a water-soluble polymer wherein some of the hydrophilic substituent groups of the polymer are associated with water molecules. At a relatively low level of hydration, the partially hydrated water-soluble polymer makes a relatively small contribution to the viscosity of the composition, while at a relatively high level of hydration, the viscosity contribution of a given amount of a partially hydrated water-soluble polymer in a given medium approaches, but is less than, the maximum contribution that the amount of water-soluble polymer is capable of making in that medium when completely hydrated. It is believed that with increasing hydration, particles of the water-soluble polymer swell, an increasing number of hydrophilic substituent groups of the water-soluble polymer, including hydrophilic substituent groups within the mass of swollen water-soluble polymer, become associated with water molecules, and, as complete hydration is approached, the water-soluble polymer chains progressively unfold and approach an unfolded, randomly coiled configuration.

"Non-hydrated" and "partially hydrated" are collectively referred to herein as "incompletely hydrated".

The degree of hydration of the water-soluble polymer can be characterized by viscosity measurements. For example, the viscosity of a given amount of a water-soluble polymer, in a given amount of an aqueous medium, in the presence of a given amount of a proposed hydration inhibitor component, and under given shear conditions, as described in more detail below (the "test composition"), can be compared to the viscosity of the same amount of the water-soluble polymer in the same amount of the aqueous medium in the absence of the proposed hydration inhibitor component (the "baseline composition"). If the viscosity of the test composition is equal to that of the baseline composition, then the water-soluble polymer of the test composition is deemed to be completely hydrated (and the proposed hydration inhibitor component is ineffective in the amount tested to inhibit hydration of the polymer). If the viscosity of the test composition is less than that of the baseline composition, then the water-soluble polymer of the test composition is deemed to be incompletely hydrated (and the proposed hydration inhibitor component is effective in the amount tested to inhibit hydration of the polymer).

In one embodiment, the liquid medium is an aqueous liquid medium and at least a portion of the water-soluble polymer is in the form of particles of the water-soluble polymer. In one embodiment, the liquid medium is an aqueous liquid medium, at least a portion of the water-soluble polymer is in the form of particles of the water-soluble polymer, and at least a portion of such particles are dispersed, more typically suspended, in the aqueous liquid medium. The presence of such particles in the composition of the present invention may be detected by, for example, optical microscopy.

In one embodiment, the composition of the present invention exhibits a viscosity of less than 10 Pa·s, more typically from about 0.1 to less than 10 Pa·s, and even more typically from about 0.1 to less than 5 Pa·s, at a shear rate of greater than or equal to $10 \text{ s}^{-1}$.

In one embodiment, the composition of the present invention exhibits a non-Newtonian "shear thinning" viscosity, that is, a viscosity that, within a given range of shear stress, decreases with increasing shear stress. Two general generally recognized categories of flow behavior, that is, plastic flow behavior and pseudoplastic flow behavior, each include shear thinning flow behavior.

In one embodiment, the composition of the present invention exhibits plastic flow behavior. As used herein, the term "plastic" in reference to flow behavior of a composition means the composition that exhibits a characteristic "yield strength", that is, a minimum shear stress required to initiate flow of the composition, and exhibits shear thinning behavior over some range of shear stress above the yield strength. A plastic composition exhibits no flow when subjected to shear stress below its yield strength, and flows when subjected to shear stress above its yield strength, wherein, over an intermediate range of shear stress above its yield strength, the composition typically exhibits a non-Newtonian viscosity that decreases with increasing shear stress, that is, shear thinning behavior, and, at shear stresses above the intermediate range of shear stress, the composition may exhibit a viscosity that does not vary with shear stress, that is, Newtonian flow behavior.

In one embodiment the composition of the present invention exhibits pseudoplastic flow behavior. As used herein, the term "pseudoplastic" in reference to the flow behavior of a composition means that the composition exhibits a viscosity that decreases with increasing shear stress, that is, shear thinning behavior.

In each case, a composition having plastic or pseudoplastic rheological properties resists flow at low shear stress, but that when subjected to an elevated shear stress, such as being shaken in a bottle or squeezed through an orifice, the composition flows and can be easily pumped, poured, or otherwise dispensed from a container. In general, sedimentation or storage condition is a low shear process, having a shear rate in the range of from about $10^{-6}$ reciprocal seconds (1/s or, equivalently, $s^{-1}$) to about 0.01 $s^{-1}$ and pumping or pouring is a relatively high shear process with a shear rate in the range of greater than or equal to about 1 $s^{-1}$, more typically from 100 $s^{-1}$ to 10,000 $s^{-1}$, and even more typically, from 100 $s^{-1}$ to 1,000 $s^{-1}$.

In one embodiment, the composition of the present invention comprises from about 1 pbw, or from about 1.5 pbw, or from about 2 pbw, or from greater than 2.5 pbw, to about 30 pbw, or to about 25 pbw, or to about 20 pbw, or to about 15 pbw, or to about 12 pbw, of the water-soluble polymer and exhibits a viscosity of less than or equal to about 10 Pa·s, more typically from about 0.1 to less than or equal to 10 Pa·s, and even more typically from about 0.1 to less than or equal to 5 Pa·s, at a shear rate of greater than or equal to 10 $s^{-1}$.

In one embodiment, the composition of the present invention resists sedimentation or separation under low shear stress storage conditions yet is pumpable under elevated shear stress condition. In one such embodiment, the composition of the present invention exhibits a viscosity of from about 1 to about 1000 Pa·s, more typically from 5 to about 800 Pa·s, even more typically from about 10 to about 500 Pa·s, at a shear rate of less than or equal to 0.01 $s^{-1}$ and exhibits a viscosity that is less than the viscosity exhibited at a shear rate of less than or equal to 0.01 $s^{-1}$, typically a viscosity of less than 10 Pa·s, more typically from about 0.1 to less than 10 Pa·s, and even more typically from about 0.1 to less than 5 Pa·s, at a shear rate of greater than or equal to 10 $s^{-1}$, more typically, greater than or equal to 100 $s^{-1}$.

In one embodiment, the composition of the present invention exhibits a viscosity greater than or equal to 10 Pa·s at a shear rate of less than or equal to 0.01 $s^{-1}$ and exhibits a viscosity of less than 10 Pa·s at a shear rate of greater than or equal to 10 $s^{-1}$, more typically, greater than or equal to 100 $s^{-1}$.

In one embodiment, the composition of the present invention exhibits a viscosity greater than or equal to 5 Pa·s at a shear rate of less than or equal to 0.01 $s^{-1}$ and exhibits a viscosity of less than 5 Pa·s at a shear rate of greater than or equal to 10 $s^{-1}$, more typically, greater than or equal to 100 $s^{-1}$.

In one embodiment, the composition of the present invention exhibits a viscosity greater than or equal to 1 Pa·s at a shear rate of less than or equal to 0.01 $s^{-1}$ and exhibits a viscosity of less than 1 Pa·s at a shear rate of greater than or equal to 10 $s^{-1}$, more typically, greater than or equal to 100 $s^{-1}$.

In one embodiment, the composition exhibits a yield strength of greater than 0 Pa, more typically greater than 0.01 Pa, even more typically from about 0.01 to about 10 Pa, still more typically from about 0.1 to about 5 Pa.

In one embodiment, the composition of the present invention also exhibits thixotropic properties. As used herein, the term "thixotropic" in reference to the flow properties of a composition means that the composition exhibits non-Newtonian shear thinning viscosity that is time dependent, i.e., the decrease in the viscosity of the composition that is brought about by increasing shear stress is reversible and the composition returns to its original state when the shear stress is discontinued.

In one embodiment, the composition of the present invention further comprises a suspending agent, typically dispersed in the liquid medium, in an amount effective to impart shear thinning viscosity, to impart yield strength, or to impart shear thinning viscosity and yield strength to the composition, generally in an amount, based on 100 pbw of the composition of the present invention, of from greater than 0 to about 10 pbw, more typically from about 0.2 to about 5 pbw, and even more typically, from about 0.5 to about 5 pbw of the suspending agent.

In one embodiment, the suspending agent is selected from silica, more typically fumed silica, inorganic colloidal or colloid-forming particles, more typically clays, rheology modifier polymers, and mixtures thereof. In one embodiment, wherein the liquid medium is an aqueous medium, the suspending agent comprises a polysaccharide polymer that differs from the water-soluble polymer and that is more readily hydrolyzed than the water-soluble polymer. For example, xanthan gum may be dissolved in an aqueous medium and used as a suspending agent to suspend incompletely hydrolyzed guar particles in the aqueous medium.

In one embodiment, wherein the liquid medium is an aqueous medium and the water-soluble polymer is incompletely hydrolyzed and itself performs the function of suspending agent by forming a water swollen, viscous mass, said viscous mass having a lower viscosity than would the same amount of the same water-soluble polymer in a fully hydrated state, and a separate suspending agent is not required.

In one embodiment, the composition of the present invention further comprises a hydration inhibitor component, typically dissolved in the liquid medium, in an amount effective to inhibit hydration of the water-soluble polysaccharide in the liquid medium so that the polysaccharide polymer component of the composition of the present invention is incompletely hydrated, generally in an amount, based on 100 pbw of the aqueous medium, of from greater than 0 to about 70 pbw, more typically from about 15 to about 60 pbw, and even more typically, from about 20 to about 50 pbw of the hydration inhibitor component. Use of a hydration inhibitor component is typically of most benefit in those embodiments of the composition of the present invention wherein the liquid medium is an aqueous medium.

In another embodiment, the hydration inhibitor component is present in an amount having a lower limit of, based on 100 pbw of aqueous solution, of 10 pbw, or in another embodiment of 15 pbw, or in another embodiment, 20 pbw, or in another embodiment, 25 pbw.

In a further embodiment, the hydration inhibitor component is present in an amount having an upper limit of, based on 100 pbw of aqueous solution, of 30 pbw, or in another embodiment of 40 pbw, or in another embodiment, 50 pbw, or in another embodiment, 60 pbw, or in another embodiment, 70 pbw.

In one embodiment, the hydration inhibitor component is selected from comprising choline chloride, potassium phosphate (dibasic) or a combination thereof.

The hydration inhibitor component can also comprise in other embodiments, surfactants, water-soluble non-surfactant salts, water dispersible organic solvents, and mixtures thereof. The terminology "non-surfactant salts" as used herein means salts that are not anionic, cationic, zwitterionic or amphoteric surfactants and includes active ingredients, such as a pesticidal active ingredient or a pharmaceutical active ingredient, that are salts and whose primary activity is other than modification of interfacial surface tension. The terminology "water dispersible organic solvents" includes water miscible organic liquids and water immiscible organic liquids that may be dispersed in water, such as for example, in the form of an emulsion of the water immiscible organic liquid in water.

It will be appreciated that the suspending agent and/or the hydration inhibitor component of the composition of the present invention may each perform more than one function. For example, a surfactant compound that functions as a hydration inhibitor component in the composition of the present invention may also perform a desired function, for example, detergency, in an end use application, such as a cleaning composition, or a salt that functions as a hydration inhibitor component in the composition of the present invention may also perform a desired function, for example, biological activity, in an end use application, such as a pharmaceutical or pesticide composition.

In one embodiment, the composition of the present invention comprises, based on 100 pbw of the composition, of from greater than 0 pbw, more typically from about 1 pbw, even more typically from about 2 pbw, and still more typically from greater than 2.5 pbw, to about 30 pbw, more typically to about 25, even more typically to about 20 pbw, and still more typically about 12 pbw, of the water-soluble polymer.

In another embodiment, the water-soluble polymer is present in an amount having a lower limit, based on 100 pbw of aqueous solution or composition, of 1 pbw, or in another embodiment of 1.2 pbw, or in another embodiment, 1.4 pbw, or in another embodiment, 1.6 pbw, or in another embodiment, 1.8 pbw, or in yet another further embodiment, 2 pbw, or in another embodiment, 2.4 pbw, or in a further embodiment, 3 pbw, or in another embodiment, 3.5 pbw, or in another embodiment, 3.8 pbw, or in another embodiment, 4 pbw, or in another embodiment, 4.5 pbw, or one embodiment, 5 pbw, or in another embodiment, 7 pbw, or in a further embodiment, 8 pbw, or in another embodiment, 10 pbw, or in yet another embodiment, 12 pbw, or in another embodiment, 16 pbw, or in another embodiment, 20 pbw. In one particular embodiment, the water-soluble polymer is present in an amount having a lower limit, based on 100 pbw of aqueous solution or composition, of 1.8 pbw. In one particular embodiment, the water-soluble polymer is present in an amount having a lower limit, based on 100 pbw of aqueous solution or composition, of 3.8 pbw. In one particular embodiment, the water-soluble polymer is present in an amount having a lower limit, based on 100 pbw of aqueous solution or composition, of 4 pbw. In one particular embodiment, the water-soluble polymer is present in an amount having a lower limit, based on 100 pbw of aqueous solution or composition, of 2 pbw.

In yet another embodiment, the water-soluble polymer is present in an amount having am upper limit, based on 100 pbw of aqueous solution or composition, of 20 pbw, or in another embodiment of 18 pbw, or in another embodiment, 17 pbw, or in another embodiment, 16 pbw, or in another embodiment, 14 pbw, or in yet another further embodiment, 13 pbw, or in another embodiment, 12 pbw, or in a further embodiment, 10 pbw, or in another embodiment, 9 pbw, or in another embodiment, 8 pbw, or in another embodiment, 7 pbw, or in another embodiment, 6 pbw, or one embodiment, 5.5 pbw, or in another embodiment, 5 pbw, or in a further embodiment, 4.5 pbw, or in another embodiment, 3 pbw, or in yet another embodiment, 2.5 pbw, or in another embodiment, 2.2 pbw. In one particular embodiment, the water-soluble polymer is present in an amount having an upper limit, based on 100 pbw of aqueous solution or composition, of 12 pbw. In one particular embodiment, the water-soluble polymer is present in an amount having an upper limit, based on 100 pbw of aqueous solution or composition, of 8 pbw. In one particular embodiment, the water-soluble polymer is present in an amount having an upper limit, based on 100 pbw of aqueous solution or composition, of 20 pbw.

In one embodiment, the polymer is a polysaccharide polymer. Polysaccharide polymer typically have a large number of hydrophilic, typically, hydroxyl, substituent groups, per molecule, more typically one or more hydroxyl group per monomeric unit of the polysaccharide polymer.

In one embodiment, wherein the polysaccharide polymer is a polymer having a weight average molecular weight of up to about 10,000,000 grams per mole (g/mol) more typically of up to about 5,000,000 grams per mole, more typically from about 100,000 to about 4,000,000 g/mol, even more typically from about 500,000 to about 3,000,000 g/mol, the composition of the present invention comprises, based on 100 pbw of the composition, up to about 15 pbw, more typically from about 1 to about 12 pbw, and even more typically, from about 2 to about 10 pbw, and still more typically from greater than 2.5 to about 8 pbw, of the polysaccharide polymer. The weight average molecular weight of a polysaccharide polymer may be determined by known methods, such as by gel permeation chromatography with light scattering or refractive index detection. As generally used herein, i.e., in the absence of an explicit limitation such as "derivatized" or "non-derivatized", the term "guar polymer" refers collectively to non-derivatized polysaccharide polymers and derivatized polysaccharide polymers.

In one embodiment, wherein the polysaccharide polymer is a depolymerized guar having a molecular weight of less than about 100,000 g/mol, the composition of the present invention comprises, based on 100 pbw of the composition, up to about 50 pbw or to about 30 pbw, more typically from about 0.1 pbw or from about 1 pbw to about 25 pbw, even more typically, from about 1.5 to about 20 pbw, still more typically from about 2 pbw to about 15 pbw, and still more typically greater than 2.5 pbw to about 12 pbw, of the polysaccharide polymer.

In one embodiment, the composition of the present invention comprises from greater than 2.5 to about 8 pbw of a guar polymer suspended in a liquid medium, more typically an aqueous medium, wherein the polymer has a weight average molecular weight of from about 100,000 g/mol, more typically from about 500,000 g/mol, to about 5,000,000 g/mol, more typically to about 4,000,000 g/mol, and even more typically to about 3,000,000 g/mol, and the composition exhibits a viscosity of greater than or equal to 5 Pa·s, more typically greater than or equal to 10 Pa·s, at a shear rate of less than 0.01 s$^{-1}$, more typically less than 0.001 s$^{-1}$, and a viscosity that is less than the viscosity exhibited at a shear rate of less than or equal to 0.01 s$^{-1}$, typically a viscosity of less than 10 Pa·s, more typically less than 5 Pa·s, at a shear rate of greater than 10 s$^{-1}$, more typically greater than 100 s$^{-1}$.

In one embodiment, the composition of the present invention comprises:
(a) a liquid medium,
(b) an incompletely hydrated water-soluble polymer, more typically wherein at least a portion of a water-soluble polymer is in the form of particles of the water-soluble polymer, at least a portion of which are dispersed, more typically suspended in the liquid medium, and
(c) a suspending agent in an amount effective to impart shear thinning properties to the composition; and
(d) a hydration inhibitor component.

In one embodiment, the liquid medium is an aqueous medium and composition of the present invention comprises, based on 100 pbw of the composition:
(a) greater than 0 pbw, more typically greater than or equal to about 10 pbw, even more typically greater than or equal to about 30 pbw, and still more typically greater than or equal to about 40 pbw water,
(b) from greater than 0 pbw, more typically from about 0.1 pbw or from about 1 pbw, more typically from about 1.5 pbw, even more typically from about 2 pbw, and still more typically from greater than 2.5 pbw, or from about 3 pbw or from about 4 pbw, to about 50 pbw or to about 30 pbw, more typically to about 25 pbw, more typically to about 20 pbw, even more typically to about 15 pbw, and still more typically, to about 12 pbw, of the incompletely hydrated water-soluble polysaccharide polymer, more typically wherein at least a portion of the water-soluble polymer is in the form of particles, and at least a portion of such particles are dispersed, more typically, suspended, in the liquid medium, and
(c) from greater than 0 pbw, more typically from about 0.1 pbw, even more typically from about 0.2 pbw, and still more typically from about 0.5 pbw, to about 10 pbw and, more typically, to about 5 pbw, of the suspending agent.

In one embodiment, the composition of the present invention comprises:
(a) an aqueous medium,
(b) an incompletely hydrated water-soluble polysaccharide polymer, more typically wherein at least a portion of a water-soluble polymer is in the form of particles of the water-soluble polymer, at least a portion of which are dispersed, more typically suspended in the aqueous medium,
(c) a suspending agent in an amount effective to impart shear thinning properties to the composition, and
(d) a hydration inhibitor component in an amount effective to inhibit hydration of the water-soluble polysaccharide in the aqueous medium.

In one embodiment, the composition of the present invention comprises, based on 100 pbw of the composition:
(a) greater than 0 pbw, more typically greater than or equal to about 10 pbw, even more typically greater than or equal to about 30 pbw, and still more typically greater than or equal to about 40 pbw, water,
(b) from greater than 0 pbw, more typically from about 0.1 pbw or from about 1 pbw, more typically from about 1.5 pbw, even more typically from about 2 pbw, and still more typically from greater than 2.5 pbw, or from about 3 pbw or from about 4 pbw, to about 50 pbw or to about 30 pbw, more typically to about 25 pbw, more typically to about 20 pbw, even more typically to about 15 pbw, and still more typically, to about 12 pbw, of the incompletely hydrated polysaccharide polymer, more typically wherein at least a portion of the water-soluble polymer is in the form of particles, and at least a portion of such particles are dispersed, more typically, suspended, in the liquid medium,
(c) from greater than 0 pbw, more typically from about 0.1 pbw, even more typically from about 0.2 pbw, and still more typically from about 0.5 pbw, to about 10 pbw and, and more typically to about 5 pbw, of the suspending agent, and
(d) from greater than 0 pbw, more typically from about 10 pbw, even more typically from about 15 pbw, and still more typically from about 20 pbw, to about 70 pbw, more typically to about 60 pbw, and even more typically to about 50 pbw, of the hydration inhibitor component.

In one embodiment, the composition of the present invention comprises, based on 100 pbw of the composition:
(a) greater than 0 pbw, more typically greater than or equal to about 10 pbw, even more typically greater than or equal to about 30 pbw, and still more typically greater than or equal to about 40 pbw, water,
(b) from greater than 0 or from about 0.1 pbw to about 50 pbw or to about 30 pbw, more typically from about 1 to about 25 pbw, more typically, from about 1.5 to about 20 pbw, even more typically, from about 2 to about 15 pbw, and still more typically from greater than 2.5 to about 12 pbw, of the incompletely hydrated polysaccharide polymer, more typically wherein at least a portion of the water-soluble polymer is in the form of particles, and at least a portion of such particles are dispersed, more typically, suspended, in the liquid medium,
(c) from greater than 0 to about 10 pbw, more typically from about 0.1 to about 10 pbw, even more typically from about 0.2 to about 5 pbw, and still more typically, from about 0.5 to about 5 pbw, of the suspending agent, and
(d) from greater than 0 to about 70 pbw, more typically from about 10 to about 70 pbw, even more typically from about 15 to about 60 pbw, and still more typically from about 20 to about 50 pbw, of the hydration inhibitor component.

In one embodiment, the suspending agent is a silica and the hydration inhibitor component is choline chloride, potassium phosphate (dibasic), or a combination thereof. The hydration inhibitor component can further comprise a non-surfactant salt, a surfactant, a water dispersible organic solvent, a mixture of a non-surfactant salt and a surfactant, a mixture of a non-surfactant salt and a water dispersible organic solvent, or a mixture of a non-surfactant salt, a surfactant, and a water dispersible organic solvent.

In one embodiment, the suspending agent is a silica and the hydration inhibitor component is choline chloride. In one embodiment, the suspending agent is a clay and the hydration inhibitor component is choline chloride.

In one embodiment, the suspending agent is a clay and the hydration inhibitor component is potassium phosphate (dibasic). In one embodiment, the suspending agent is a silica and the hydration inhibitor component is potassium phosphate (dibasic). In another embodiment, the hydration inhibitor component further comprises a non-surfactant salt, a surfactant, a water dispersible organic solvent, a mixture of a non-surfactant salt and a surfactant, a mixture of a non-surfactant salt and a water dispersible organic solvent, or a mixture of a non-surfactant salt, a surfactant, and a water dispersible organic solvent.

In one embodiment, the suspending agent is a mixture of a silica and a clay

In one embodiment, the composition of the present invention comprises, based on 100 pbw of the composition:
from greater than 0 pbw, or greater than or equal to about 10 pbw, of or greater than or equal about 30 pbw of an aqueous medium, more typically water or a mixture of water and a water miscible organic liquid,
from greater than 2.5 pbw, or from about 3 pbw, or from about 4 pbw to about 50 pbw, or to about 30 pbw, or to about 25 pbw, or to about 20 pbw, or to about 15 pbw, or to about 12 pbw, of a water-soluble polymer, more typically a water-soluble polymer selected from water-soluble polysaccharide polymers and water-soluble non-polysaccharide polymers, and even more typically a water-soluble polymer selected from polyacrylamide polymers, non-derivatized guars, derivatized guars, and mixtures thereof, wherein such water-soluble polymer is incompletely hydrated, more typically wherein at least a portion of the water-soluble polymer is in the form of particles and at least a portion of such particles are dispersed, more typically, suspended, in the liquid medium, from 0 pbw, or from greater than 0 pbw, or from about 0.1 pbw, or from about 0.2 pbw, or from about 0.5 pbw, to about 10 pbw, or to about 5 pbw, of a suspending agent, more typically of a suspending agent selected from silicas, inorganic colloidal or colloid-forming particles, rheology modifier polymers, water-soluble polymers other than the water-soluble polymer, and mixtures thereof dissolved or dispersed in the liquid medium, and from 0 pbw, or from greater than 0 pbw, or from about 2 pbw, or from about 5 pbw, to about 30 pbw or to about 15 pbw, or to about 10 pbw, of a hydration inhibitor component, more typically a hydration inhibitor component selected from surfactants, water-soluble non-surfactant salts, water dispersible organic solvents, and mixtures thereof dissolved or dispersed in the liquid medium.

In one embodiment, the composition of the present invention comprises, based on 100 parts by weight of the composition:

from greater than 0 pbw, or greater than or equal to about 10 pbw, or greater than or equal to about 30 pbw an aqueous liquid medium comprising a mixture of water and a water immiscible organic liquid, an emulsifier, more typically one or more emulsifiers comprising a nonionic surfactant, even more typically comprising a nonionic surfactant selected from sorbitan fatty acid esters, aryl alkoxylates, alkoxylated fatty alcohols, alkoxylated fatty acids, alkoxylated triglycerides, alkoxy copolymers, alkylpolyglucosides, alkoxylated fatty amines, and ether amines, and, and mixtures thereof, in an amount effective to emulsify the water and water immiscible organic liquid, more typically from greater than 0 pbw, or from about 2 pbw, to about 8 pbw or to about 6 pbw, of the surfactant, from 0 pbw, or from greater than 0 pbw, or from about 0.1 pbw, or from about 1 pbw, or from about 1.5 pbw, or from about 2 pbw, or from greater than 2.5 pbw, or from about 4 pbw, to about 50 pbw to about 30 pbw, or to about 25 pbw, or to about 20 pbw, or to about 15 pbw, or to about 12 pbw, of a first water-soluble polymer, more typically a water-soluble polymer selected from water-soluble polysaccharide polymers and water-soluble non-polysaccharide polymers, and even more typically a water-soluble polymer selected from polyacrylamide polymers, non-derivatized guars, derivatized guars, and mixtures thereof, wherein such water-soluble polymer is incompletely hydrated, more typically wherein at least a portion of the water-soluble polymer is in the form of particles of the water-soluble polymer and wherein at least a portion of such particles is dispersed, more typically, suspended, in the liquid medium, from 0 pbw, or from greater than 0 pbw, or from about 0.1 pbw, or from about 0.2 pbw, or from about 0.5 pbw, to about 10 pbw, or to about 5 pbw, of a suspending agent selected from silicas, inorganic colloidal or colloid-forming particles, rheology modifier polymers, second water-soluble polymers other than the selected first water-soluble polymer, and mixtures thereof dissolved or dispersed in the liquid medium, and from 0 pbw, or from greater than 0 pbw, or from about 2 pbw, or from about 5 pbw, to about 30 pbw or to about 15 pbw, or to about 10 pbw, of a hydration inhibitor component hydration inhibitor component selected from surfactants, water-soluble non-surfactant salts, water dispersible organic solvents, and mixtures thereof dissolved or dispersed in the liquid medium, wherein the composition is in the form of an emulsion, a microemulsion, or a suspoemulsion.

In one embodiment, the composition of the present invention comprises, based on 100 parts by weight of the composition:

from greater than 0 pbw, or greater than or equal to about 10 pbw, or greater than or equal to about 30 pbw of a non-aqueous liquid medium, more typically of a water immiscible organic liquid, from greater than 0 pbw, or from about 0.1 pbw, or from about 1 pbw, or from about 1.5 pbw, or from about 2 pbw, or from greater than 2.5 pbw, or from about 4 pbw, to about 50 pbw, or to about 30 pbw, or to about 25 pbw, or to about 20 pbw, or to about 15 pbw, or to about 12 pbw, of a water-soluble polymer, more typically a water-soluble polymer selected from water-soluble polysaccharide polymers and water-soluble non-polysaccharide polymers, and even more typically a water-soluble polymer selected from polyacrylamide polymers, non-derivatized guars, derivatized guars, and mixtures thereof, wherein at least a portion of the water-soluble polymer is in the form of particles and at least a portion of such particles are dispersed, more typically, suspended, in the non-aqueous liquid medium, and from 0 pbw, or from greater than 0 pbw, or from about 0.1 pbw, or from about 0.2 pbw, or from about 0.5 pbw, to about 10 pbw or to about 5 pbw, of a suspending agent, more typically a suspending agent selected from selected from silicas, inorganic colloidal or colloid-forming particles, and mixtures thereof, dispersed in the non-aqueous liquid medium.

Suitable water-soluble polysaccharide polymers are include, for example, galactomannans such as guars, including guar derivatives, xanthans, polyfructoses such as levan, starches, including starch derivatives, such as amylopectin, and cellulose, including cellulose derivatives, such as methylcellulose, ethylcellulose, carboxymethylcellulose, hydroxyethylcellulose, cellulose acetate, cellulose acetate butyrate, and cellulose acetate propionate.

Galactomannans are polysaccharides consisting mainly of the monosaccharides mannose and galactose. The mannose-elements form a chain consisting of many hundreds of (1,4)-β-D-mannopyranosyl-residues, with 1,6 linked α-D-galactopyranosyl-residues at varying distances, dependent on the plant of origin. Naturally occurring galactomannans are available from numerous sources, including guar gum, guar splits, locust bean gum and tara gum. Additionally, galactomannans may also be obtained by classical synthetic routes or may be obtained by chemical modification of naturally occurring galactomannans.

Guar gum refers to the mucilage found in the seed of the leguminous plant *Cyamopsis tetragonolobus*. The water-soluble fraction (85%) is called "guaran," which consists of linear chains of (1,4)-.β-D mannopyranosyl units—with α-D-galactopyranosyl units attached by (1,6) linkages. The ratio of D-galactose to D-mannose in guaran is about 1:2. Guar gum typically has a weight average molecular weight of between 2,000,000 and 5,000,000 g/mol. Guars having a reduced molecular weight, such as for example, from about 50,000 to about 2,000,000 g/mol are also known.

Guar seeds are composed of a pair of tough, non-brittle endosperm sections, hereafter referred to as "guar splits," between which is sandwiched the brittle embryo (germ). After dehulling, the seeds are split, the germ (43-47% of the seed) is removed by screening, and the splits are ground. The ground splits are reported to contain about 78-82% galactomannan polysaccharide and minor amounts of some proteinaceous material, inorganic non-surfactant salts, water-insoluble gum, and cell membranes, as well as some residual seedcoat and embryo.

Locust bean gum or carob bean gum is the refined endosperm of the seed of the carob tree, *Ceratonia siliqua*. The ratio of galactose to mannose for this type of gum is about 1:4. Locust bean gum is commercially available.

Tara gum is derived from the refined seed gum of the tara tree. The ratio of galactose to mannose is about 1:3. Tara gum is commercially available.

Other galactomannans of interest are the modified galactomannans, including derivatized guar polymers, such as carboxymethyl guar, carboxymethylhydroxypropyl guar, cationic hydroxypropyl guar, hydroxyalkyl guar, including hydroxyethyl guar, hydroxypropyl guar, hydroxybutyl guar and higher hydroxylalkyl guars, carboxylalkyl guars, including carboxymethyl guar, carboxylpropyl guar, carboxybutyl guar, and higher carboxyalkyl guars, the hydroxyethylated, hydroxypropylated and carboxymethylated derivative of guaran, the hydroxethylated and carboxymethylated derivatives of carubin, and the hydroxypropylated and carboxymethylated derivatives of cassia-gum. In one embodiment, the derivatized guar is hydroxypropyl guar. In one embodiment, the derivatized guar is cationic hydroxypropyl guar or cationic guar.

Xanthans of interest are xanthan gum and xanthan gel. Xanthan gum is a polysaccharide gum produced by *Xathomonas campestris* and contains D-glucose, D-mannose, D-glucuronic acid as the main hexose units, also contains pyruvate acid, and is partially acetylated.

Levan is a polyfructose comprising 5-membered rings linked through β-2,6 bonds, with branching through β-2,1 bonds. Levan exhibits a glass transition temperature of 138° C. and is available in particulate form. At a molecular weight of 1-2 million, the diameter of the densely-packed spherulitic particles is about 85 nm.

Modified celluloses are celluloses containing at least one functional group, such as a hydroxy group, hydroxycarboxyl group, or hydroxyalkyl group, such as for example, hydroxymethyl cellulose, hydroxyethyl celluloses, hydroxypropyl celluloses or hydroxybutyl celluloses.

Processes for making derivatives of guar gum splits are generally known. Typically, guar splits are reacted with one or more derivatizing agents under appropriate reaction conditions to produce a guar polysaccharide having the desired substituent groups. Suitable derivatizing reagents are commercially available and typically contain a reactive functional group, such as an epoxy group, a chlorohydrin group, or an ethylenically unsaturated group, and at least one other substituent group, such as a cationic, nonionic or anionic substituent group, or a precursor of such a substituent group per molecule, wherein substituent group may be linked to the reactive functional group of the derivatizing agent by bivalent linking group, such as an alkylene or oxyalkylene group. Suitable cationic substituent groups include primary, secondary, or tertiary amino groups or quaternary ammonium, sulfonium, or phosphinium groups. Suitable nonionic substituent groups include hydroxyalkyl groups, such as hydroxypropyl groups. Suitable anionic groups include carboxyalkyl groups, such as carboxymethyl groups. The cationic, nonionic and/or anionic substituent groups may be introduced to the guar polysaccharide chains via a series of reactions or by simultaneous reactions with the respective appropriate derivatizing agents.

The guar may be treated with a crosslinking agent, such as for example, borax (sodium tetra borate) is commonly used as a processing aid in the reaction step of the water-splits process to partially crosslink the surface of the guar splits and thereby reduces the amount of water absorbed by the guar splits during processing. Other crosslinkers, such as, for example, glyoxal or titanate compounds, are known.

In one embodiment, the polysaccharide component of the composition of the present invention is a non-derivatized galactomannan polysaccharide, more typically a non-derivatized guar gum.

In one embodiment, the polysaccharide is a derivatized galactomannan polysaccharide that is substituted at one or more sites of the polysaccharide with a substituent group that is independently selected for each site from the group consisting of cationic substituent groups, nonionic substituent groups, and anionic substituent groups.

In one embodiment, the polysaccharide component of the composition of the present invention is derivatized galactomannan polysaccharide, more typically a derivatized guar. Suitable derivatized guars include, for example, hydroxypropyl trimethylammonium guar, hydroxypropyl lauryldimethylammonium guar, hydroxypropyl stearyldimethylammonium guar, hydroxypropyl guar, carboxymethyl guar, guar with hydroxypropyl groups and hydroxypropyl trimethylammonium groups, guar with carboxymethyl hydroxypropyl groups and mixtures thereof.

The amount of derivatizing groups in a derivatized polysaccharide polymer may be characterized by the degree of substitution of the derivatized polysaccharide polymer or the molar substitution of the derivatized polysaccharide polymer.

As used herein, the terminology "degree of substitution" in reference to a given type of derivatizing group and a given polysaccharide polymer means the number of the average number of such derivatizing groups attached to each monomeric unit of the polysaccharide polymer. In one embodiment, the derivatized galactomannan polysaccharide exhibits a total degree of substitution ("$DS_T$") of from about 0.001 to about 3.0, wherein:

$DS_T$ is the sum of the DS for cationic substituent groups ("$DS_{cationic}$"), the DS for nonionic substituent groups ("$DS_{nonionic}$") and the DS for anionic substituent groups ("$DS_{anionic}$"), $DS_{cationic}$ is from 0 to about 3, more typically from about 0.001 to about 2.0, and even more typically from about 0.001 to about 1.0, $DS_{nonionic}$ is from 0 to 3.0, more typically from about 0.001 to about 2.5, and even more typically from about 0.001 to about 1.0, and $DS_{anionic}$ is from 0 to 3.0, more typically from about 0.001 to about 2.0.

As used herein, the term "molar substitution" or "ms" refers to the number of moles of derivatizing groups per moles of monosaccharide units of the guar. The molar substitution can be determined by the Zeisel-GC method. The molar substitution utilized by the present invention is typically in the range of from about 0.001 to about 3.

In one embodiment, the polysaccharide polymer is in the form of particles. In one embodiment, the particles of polysaccharide polymer have an initial, that is, determined for dry particles prior to suspension in the aqueous medium, average particle size of about 5 to 200 µm, more typically about 20 to 200 µm as measured by light scattering, and exhibit a particle size in the aqueous medium of greater than or equal to the initial particle size, that is greater than or equal to 5 µm, more typically greater or equal to than 20 µm, with any increase from the initial particle size being due to swelling brought about by partial hydration of the polysaccharide polymer in the aqueous medium.

In one embodiment, the water-soluble polymer is a water-soluble non-polysaccharide polymer. Suitable water-soluble non-polysaccaharide polymers include, for example, lecithin polymers, poly(alkyleneoxide) polymers, such as poly(ethylene oxide) polymers, and water-soluble polymers derived from ethylenically unsaturated monomers. Suitable water-soluble polymers derived from ethylenically unsaturated monomers include water-soluble polymers derived from acrylamide, methacrylamide, 2-hydroxy ethyl acrylate, and/or N-vinyl pyrrolidone, including homopolymers of such monomers, such as poly(acrylamide) polymers and poly(vinyl pyrrolidone) polymers, as well as copolymers of such monomers with one or more comonomers. Suitable water-soluble copolymers derived from ethylenically unsaturated monomers include water-soluble cationic polymers made by polymerization of at least one cationic monomer, such as a diamino alkyl (meth)acrylate or diamino alkyl (meth)acrylamide, or mixture thereof and one or more nonionic monomers, such as acrylamide or methacrylamide. In one embodiment, the non-polysaccharide polymer exhibits a weight average molecular weight of greater than about 1,000,000 g/mol, more typically greater than about 2,000,000 g/mol to about 20,000,000 g/mol, more typically to about 10,000,000 g/mol.

In one embodiment, the suspending agent component of the composition of the present invention comprises a fumed silica. Fumed silica is typically produced by the vapor phase hydrolysis of a silicon compound, e.g., silicon tetrachloride, in a hydrogen oxygen flame. The combustion process creates silicon dioxide molecules that condense to form particles. The particles collide, attach, and sinter together. The result of these processes is typically a three dimensional branched chain aggregate, typically having an average particles size of from about 0.2 to 0.3 micron. Once the aggregates cool below the fusion point of silica (1710° C.), further collisions result in mechanical entanglement of the chains, termed agglomeration.

In one embodiment, suitable fumed silica has a BET surface area of from 50-400 square meters per gram (m$^2$/g), more typically from, from about 100 m$^2$/g to about 400 m$^2$/g.

In one embodiment, the suspending agent component of the composition of the present invention comprises a fumed silica in an amount that is effective, either alone or in combination with one or more other suspending agents, to impart shear thinning viscosity to the composition, typically in an amount, based on 100 pbw of the composition, of from greater than 0 pbw, more typically from about 0.1 pbw, and even more typically from about 0.5 pbw, to about 10 pbw, more typically to about 5 pbw, and even more typically to about 2.5 pbw, of fumed silica.

In one embodiment, the composition of the present invention comprises, based on 100 pbw of the composition, from greater than 0 to about 10 pbw, more typically from about 0.1 to about 5 pbw, and even more typically from about 0.5 to about 2.5 pbw, of fumed silica.

In one embodiment, the suspending agent component of the composition of the present invention comprises an inorganic, typically aluminosilicate or magnesium silicate, colloid-forming clay, typically, a smectite (also known as montmorillonoid) clay, an attapulgite (also known as palygorskite) clay, or a mixture thereof. These clay materials can be described as expandable layered clays, wherein the term "expandable" as used herein in reference to such clay relates to the ability of the layered clay structure to be swollen, or expanded, on contact with water.

Smectites are three-layered clays. There are two distinct classes of smectite-type clays. In the first class of smectites, aluminum oxide is present in the silicate crystal lattice and the clays have a typical formula of $Al_2(Si_2O_5)_2(OH)_2$. In the second class of smectites, magnesium oxide is present in the silicate crystal lattice and the clays have a typical formula of $Mg_3(Si_2O_5)(OH)_2$. The range of the water of hydration in the above formulas can vary with the processing to which the clay has been subjected. This is immaterial to the use of the smectite clays in the present compositions in that the expandable characteristics of the hydrated clays are dictated by the silicate lattice structure. Furthermore, atomic substitution by iron and magnesium can occur within the crystal lattice of the smectites, while metal cations such as $Na^+$, $Ca^{+2}$, as well as $H^+$, can be present in the water of hydration to provide electrical neutrality. Although the presence of iron in such clay material is preferably avoided to minimize chemical interaction between clay and optional composition components, such cation substitutions in general are immaterial to the use of the clays herein since the desirable physical properties of the clay are not substantially altered thereby.

The layered expandable aluminosilicate smectite clays useful herein are further characterized by a dioctahedral crystal lattice, whereas the expandable magnesium silicate smectite clays have a trioctahedral crystal lattice.

Suitable smectite clays, include, for example, montmorillonite (bentonite), volchonskoite, nontronite, beidellite, hectorite, saponite, sauconite and vermiculite, are commercially available.

Attapulgites are magnesium-rich clays having principles of superposition of tetrahedral and octahedral unit cell elements different from the smectites. An idealized composition of the attapulgite unit cell is given as: $(H_2O)_4(OH)_2Mg_5Si_8O_2O_4H_2O$. Attapulgite clays are commercially available.

As noted above, the clays employed in the compositions of the present invention contain cationic counter ions such as protons, sodium ions, potassium ions, calcium ions, magnesium ions and the like. It is customary to distinguish between clays on the basis of one cation which is predominately or exclusively absorbed. For example, a sodium clay is one in which the absorbed cation is predominately sodium. Such absorbed cations can become involved in exchange reactions with cations present in aqueous solutions.

Commercially obtained clay materials can comprise mixtures of the various discrete mineral entities. Such mixtures of the minerals are suitable for use in the present compositions. In addition, natural clays sometimes consist of particles in which unit layers of different types of clay minerals are stacked together (interstratification). Such clays are called mixed layer clays, and these materials are also suitable for use herein.

In one embodiment, suspending agent component of the composition of the present invention comprises an inorganic colloid forming clay in an amount that is effective, either alone or in combination with one or more other suspending agents, to impart shear thinning viscosity to the composition, typically in an amount, based on 100 pbw of the composition, of from greater than 0 pbw, more typically from about 0.1 pbw, and even more typically from about 0.5 pbw, to about 10 pbw, more typically to about 5 pbw, and even more typically to about 2.5 pbw, of inorganic colloid forming clay.

In one embodiment, the composition of the present invention comprises, based on 100 pbw of the composition, from greater than 0 to about 10 pbw, more typically from about 0.1 to about 5 pbw, and even more typically from about 0.5 to about 2.5 pbw, of inorganic colloid forming clay.

A fumed silica or clay suspending agent is typically introduced to the liquid medium and mixed to disperse the fumed silica or clay suspending agent in the liquid medium.

In one embodiment, the suspension agent component of the composition of the present invention comprises a rheology modifier polymer. Rheology modifier polymers are polymers used to thicken aqueous compositions. Suitable rheology modifier polymers are known and typically fall within one of three general classes, that is, alkali swellable polymers, hydrogen bridging rheology modifiers, and hydrophobic associative thickeners.

Alkali swellable polymers are pH-responsive polymers that swell when placed in an alkali medium and include, for example, homopolymers and copolymers comprising units derived from ethylenically unsaturated carboxylic acid monomers such as acrylic acid, methacrylic acid, maleic acid.

Suitable hydrogen bridging rheology modifiers include, for example, hydrocolloids such as cellulose and hydrophilic cellulose derivatives, such as carboxymethylcellulose and hydroxyethylcellulose, and natural gums and gum derivatives, such as guar gum, hydroxypropyl guar, xanthan gun, Rheozan, and carrageenan. In one embodiment, the hydrogen bridging rheology modifier is a second water-soluble polymer that is different from the incompletely hydrated water-soluble polymer component of the composition of the present invention. For example, in an embodiment wherein the incompletely hydrated water-soluble polymer is a first polysaccharide polymer, the hydrogen bridging rheology modifier may be a second polysaccharide polymer that is more readily hydrated than the first polysaccharide polymer.

Suitable hydrophobic associative rheology modifiers are known and include hydrophobically modified natural or synthetic polymers that contain both hydrophobic and hydrophilic substituent groups, such as hydrophobically modified cellulose derivatives and polymers having a synthetic hydrophilic polymer backbone, such as a poly(oxyalkylene), such as a poly(oxyethylene) or poly(oxypropylene) backbone and hydrophobic pendant groups, such as $(C_{10}-C_{30})$ hydrocarbon groups. Nonionic associate thickeners are typically preferred, due to their relative insensitivity to high salt concentrations, and include, for example, PEG-200 glyceryl tallowate, PEG-200 hydrogenated glyceryl palmate, PPG-14 palmeth-60 hexyl dicarbamate, PEG-160 sorbitan triisostearate.

In one embodiment, the suspending agent component of the composition of the present invention comprises a rheology modifier polymer in an amount that is effective, either alone or in combination with one or more other suspending agents, to impart shear thinning viscosity to the composition, typically in an amount, based on 100 pbw of the composition, of from greater than 0 pbw, more typically from about 0.1 pbw, and even more typically from about 1 pbw, to about 10 pbw, more typically to about 5 pbw, of rheology modifier polymer.

In one embodiment, the composition of the present invention comprises, based on 100 pbw of the composition, from greater than 0 to about 10 pbw, more typically from about 0.1 to about 10 pbw, and even more typically from about 1 to about 5 pbw, of rheology modifier polymer.

An rheology modifier suspending agent is typically introduced to the liquid medium and subjected mixing to disperse the rheology modifier polymer in the aqueous medium.

In one embodiment, the composition of the present invention further comprises a surfactant. As used herein the term "surfactant" means a compound that is capable of lowering the surface tension of water, more typically, a compound selected from one of five classes of compounds, that is, cationic surfactants, anionic surfactants, amphoteric surfactants, zwitterionic surfactants, and nonionic surfactants, as well as mixtures thereof, that are known for their detergent properties. In one embodiment, the hydration inhibitor component of the composition of the present invention further comprises a surfactant.

Suitable cationic surfactants are known in the art, and include, for example, amine salts, such as, ethoxylated tallow amine, cocoalkylamine, and oleylamine, quaternary ammonium compounds such as cetyl trimethyl ammonium bromide, myristyl trimethyl ammonium bromide, stearyl dimethyl benzyl ammonium chloride, lauryl/myristryl trimethyl ammonium methosulfate, stearyl octyldimonium methosulfate, dihydrogenated palmoylethyl hydroxyethylmonium methosulfate, isostearyl benzylimidonium chloride, cocoyl benzyl hydroxyethyl imidazolinium chloride, cocoyl hydroxyethylimidazolinium, and mixtures thereof.

In one embodiment, the hydration inhibitor component of the composition of the present invention comprises an anionic surfactant. Suitable anionic surfactants are known in the art, and include, for example, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and mixtures thereof.

In one embodiment, the hydration inhibitor component of the composition of the present invention comprises an amphoteric surfactant. Suitable amphoteric surfactants are known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxyl, sulfonate, sulfate, phosphate, or phosphonate. In one embodiment, the amphoteric surfactant comprises at least one compound selected from cocoamphoacetate, cocoamphodiacetate, lauroamphoacetate, and lauroamphodiacetate.

In one embodiment, the hydration inhibitor component of the composition of the present invention comprises a zwitterionic surfactant. Suitable zwitterionic surfactants are known in the art, and include, for example, those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxyl, sulfonate, sulfate, phosphate or phosphonate. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxyethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, alkyl amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines.

In one embodiment, the hydration inhibitor component of the composition of the present invention comprises a nonionic surfactant. Suitable nonionic surfactants are known in the art, and include, for example, long chain alkyl glucosides having alkyl groups containing about 8 carbon atoms to about 22 carbon atoms, coconut fatty acid monoethanolamides such as cocamide MEA, coconut fatty acid diethanolamides, alcohol alkoxylates, and mixtures thereof.

In one embodiment, the hydration inhibitor component of the composition of the present invention comprises a mixture of two or more surfactants selected from cationic surfactants, anionic surfactants, amphoteric surfactants, zwitterionic surfactants, nonionic surfactants, and mixtures thereof.

In one embodiment, the hydration inhibitor component of the composition of the present invention comprises a surfactant in an amount that is effective, either alone or in combination with one or more other hydration inhibitor components, to prevent or to at least inhibit hydration of the polysaccharide, typically in an amount, based on 100 pbw of the composition, of from greater than 0 pbw, more typically from about 2 pbw, and even more typically from about 5 pbw, to about 60 pbw, more typically to about 50 pbw, and even more typically, to about 40 pbw, of surfactant.

In one embodiment, the composition of the present invention comprises, based on 100 pbw of the composition, from greater than 0 to about 60 pbw, more typically from about 2 to about 50 pbw, and even more typically, from about 5 to about 40 pbw, of surfactant.

In one embodiment, the hydration inhibitor component as described herein comprises choline chloride, potassium phosphate (dibasic), or a combination thereof. In another embodiment, the hydration inhibitor component comprises choline chloride, choline bicarbonate, choline dihydrogen citrate, choline bitarate, potassium hydrogen phosphate, potassium carbonate, potassium phosphate (dibasic), or any combination thereof. In another embodiment, the hydration inhibitor component further comprises a water-soluble non-surfactant salt. Suitable water-soluble non-surfactant salts include organic non-surfactant salts, inorganic non-surfactant salts, and mixtures thereof, as well as polyelectrolytes, such as uncapped polyacrylates, polymaleates, or polycarboxylates, lignin sulfonates or naphthalene sulfonate formaldehyde copolymers. The water-soluble non-surfactant salt comprises a cationic component and an anionic component. Suitable cations may be monovalent or multivalent, may be organic or inorganic, and include, for example, sodium, potassium, lithium, calcium, magnesium, cesium, and lithium cations, as well as mono-, di- tri- or quaternary ammonium or pyridinium cation. Suitable anions may be a monovalent or multivalent, may be organic or inorganic, and include, for example, chloride, sulfate, nitrate, nitrite, carbonate, citrate, cyanate acetate, benzoate, tartarate, oxalate, carboxylate, phosphate, and phosphonate anions. Suitable water-soluble non-surfactant salts include, for example, non-surfactant salts of multivalent anions with monovalent cations, such as potassium pyrophosphate, potassium tripolyphosphate, and sodium citrate, non-surfactant salts of multivalent cations with monovalent anions, such as calcium chloride, calcium bromide, zinc halides, barium chloride, and calcium nitrate, and non-surfactant salts of monovalent cations with monovalent anions, such as sodium chloride, potassium chloride, potassium iodide, sodium bromide, ammonium bromide, ammonium sulfate, alkali metal nitrates, and ammonium nitrates.

In one embodiment, the composition of the present invention does not contain any cationic surfactant, anionic surfactant, amphoteric surfactant, zwitterionic surfactant that is a water-soluble salt.

In one embodiment, the composition of the present invention comprises a cationic surfactant, anionic surfactant, amphoteric surfactant, or zwitterionic surfactant, such as, for example, sodium lauryl sulfate, that is a water-soluble salt. The amount of surfactant that is a water-soluble salt is to be included in the total amount of water-soluble salt for purposes of determining the total amount of water-soluble salt component of the composition of the present invention.

As discussed, below, in one embodiment, the composition is a concentrated, dilutable form of an end use composition and further comprises one or more active ingredients, such as, for example, a personal care benefit agent, a pesticidal active ingredient, or a pharmaceutical active ingredient, appropriate to the intended end use. Such active ingredients may be water-soluble non-surfactant salts. The amount of active ingredient that is a water-soluble non-surfactant salt is to be included in the total amount of water-soluble for purposes of determining the total amount of water-soluble salt component of the composition of the present invention.

In one embodiment, the composition of the present invention comprises a water-soluble salt in an amount that is effective, either alone or in combination with one or more other hydration inhibitor components, to prevent or to at least inhibit hydration of the polysaccharide, typically in an amount, based on 100 pbw of the composition and including the amount of any water-soluble non-surfactant salt, the amount of any of the surfactant component of the composition of the present invention that is a water-soluble salt and the amount of any of the active ingredient component of the composition of the present invention that is a water-soluble salt, of from greater than 0 pbw, more typically, from about 2 pbw and even more typically, from about 5 pbw, to about 70 pbw, more typically to about 65 pbw and even more typically, to about 60 pbw, of water-soluble salt.

In one embodiment, the composition of the present invention comprises, based on 100 pbw of the composition and including the amount of any water-soluble non-surfactant salt, the amount of any of the surfactant component of the composition of the present invention that is a water-soluble and the amount of any active ingredient component of the composition of the present invention that is a water-soluble salt, from greater than 0 to about 70 pbw, more typically, from about 2 to about 65 pbw and even more typically, from about 5 to about 60 pbw, of water-soluble salt.

In one embodiment, the hydration inhibitor component of the composition of the present invention comprises a water dispersible organic solvent. Suitable water dispersible organic solvents include, for example, $(C_1-C_{18})$alcohols, such as, for example, monohydric alcohols, such as methanol, ethanol, isopropanol, cetyl alcohol, stearyl alcohol, benzyl Alcohol, oleyl alcohol, and polyhydric alcohols, such as, for example, 2-butoxyethanol, ethylene glycol, and glycerol, alkylether diols such as, for example, ethylene glycol monoethyl ether, propylene glycol monoethyl ether, and diethylene glycol monomethyl ether, and mixtures thereof.

In one embodiment, the hydration inhibitor component of the composition of the present invention comprises a water dispersible, more typically, water-soluble, organic solvent. Suitable water dispersible organic solvents include, for example, monohydric alcohols, polyhydric alcohols, alkylether diols, and mixtures thereof.

In one embodiment, the composition of the present invention comprises a water dispersible organic solvent, in an amount that is effective, either alone or in combination with one or more other hydration inhibitor components, to prevent or to at least inhibit hydration of the polysaccharide, typically in an amount, based on 100 pbw of the composition, of from greater than 0 pbw, more typically from about 2 pbw, and even more typically, from about 5 pbw to about 40 pbw, more typically to about 30 pbw, and even more typically to about 25 pbw, of water dispersible organic solvent.

In one embodiment, the composition of the present invention comprises, based on 100 pbw of the composition, from greater than 0 to about 40 pbw, more typically from about 2 to about 30 pbw, and even more typically, from about 5 to about 25 pbw, of water dispersible organic solvent.

The composition of the present invention is typically made by mixing the components of the composition together.

In one embodiment, wherein the liquid medium is an aqueous medium that comprises water or water and a water miscible organic liquid, the composition is typically made by:

mixing the hydration inhibitor component as described herein with the aqueous liquid medium, mixing the water-soluble polymer with the mixture of aqueous liquid medium, and hydration inhibitor component, and mixing the suspending agent with the mixture of the aqueous liquid medium, the hydration inhibitor component and the water-soluble polymer. This manner of addition avoids hydration of the water-soluble polymer and avoids the risk formation of an intermediate composition having an intractably high viscosity.

In another embodiment, wherein the liquid medium is an aqueous medium comprising water and a water immiscible organic liquid, the composition is typically made by:

mixing, optionally, all or a portion of the emulsifier, and optionally, a suspending agent, with the water, mixing the water-soluble polymer, optionally all or a portion of the emulsifier, and optionally, a suspending agent, with the water immiscible organic liquid, and combining the water-based mixture and the water immiscible organic liquid-based mixture to form the composition. The emulsifier may be added to either the water mixture or the water immiscible organic liquid mixture, or a portion of the emulsifier may be added to each of the mixtures. If the optional suspending agent is used, all of the suspending agent may all be added to the water, all of the suspending agent may be added to the water immiscible organic liquid, or a first portion of the suspending agent may be added to the water and a second portion of the suspending agent added to the water immiscible organic liquid. Any optional hydration inhibitor component that may be used in addition to the water immiscible organic liquid may be added to either the water or the water immiscible organic liquid. This manner of addition avoids hydration of the water-soluble polymer and avoids the risk formation of an intermediate composition having an intractably high viscosity.

In another embodiment, wherein the liquid medium is a non aqueous liquid medium, more typically a water immiscible organic liquid, the pesticide, water-soluble polymer, optional suspending agent and optional hydration inhibitor component are typically added to the non-aqueous liquid medium and mixed to form the composition.

In one embodiment, the composition of the present invention exhibits dilution thickening behavior, that is, as the composition of the present invention is diluted with water, the viscosity of the viscosity of the composition initially increases with increasing dilution, reaches a maximum value and then decreases with further dilution. The increasing viscosity with increasing dilution corresponds to an increasing concentration of dissolved water-soluble polysaccharide as the concentration of the surfactant and or salt component of the composition decreases with increasing dilution.

In one embodiment, the composition of the present invention is useful as a pumpable liquid source of polysaccharide with a high polysaccharide content for formulating aqueous end use compositions, in particular agricultural pesticide compositions.

In one embodiment, the composition of the present invention is an agricultural adjuvant composition that stable, has a low viscosity, is easily transportable, is pourable and pumpable under field conditions, and is dilutable with water under agricultural field conditions.

In one embodiment, the composition of the present invention is mixed with a pesticide active ingredient and, optionally other adjuvant ingredients, and water to form a dilute pesticide composition for spray application to target pests.

In one embodiment, the composition is a concentrated, dilutable form of an end use composition and further comprises one or more active ingredients, such as, for example, a personal care benefit agent, a pesticidal active ingredient, or a pharmaceutical active ingredient, appropriate to the intended end use. In one embodiment, the concentrate is diluted to form an end use composition, the end use composition is contacted with a target substrate, such as plant foliage, and the water-soluble polymer component of the concentrate enhances delivery of the active ingredient onto the substrate.

In one embodiment, the composition of the present invention is prepared on an as needed basis and is sufficiently stable, that is, a quiescent sample of the composition shows no evidence, by visual inspection, of gravity driven separation, such as, separation into layers and/or precipitation of components, such as, for example, incompletely hydrated water-soluble polymer, from the liquid medium, within the anticipated time period, for example, one hour, more typically two hours, between preparation and use.

In one embodiment, the composition of the present invention exhibits good storage stability and a quiescent sample of the composition shows no evidence, by visual inspection, of gravity driven separation within a given time, such as, for example, one week, more typically, one month, even more typically 3 months, under given storage conditions, such as, for example, at room temperature.

In one embodiment, the composition of the present invention exhibits good storage stability and a quiescent sample of the composition shows no evidence, by visual inspection, of gravity driven separation within a given time, such as, for example, 24 hours, more typically, four days, even more typically, one week, under accelerated aging conditions at an elevated storage temperature of up to, for example, 54° C., more typically, 45° C.

The invention claimed is:

1. A concentrated adjuvant composition, comprising, based on 100 parts by weight of the composition:

greater than 1.8 parts by weight of an incompletely hydrated water-soluble polymer suspended in a liquid medium;

a hydration inhibitor component comprising choline chloride, dibasic potassium phosphate or a combination thereof; and a suspending agent in an amount effective to impart shear thinning properties to the composition.

2. The composition of claim 1 wherein the hydration inhibitor component comprises choline chloride.

3. The composition of claim 1 wherein the hydration inhibitor component comprises dibasic potassium phosphate.

4. The composition of claim 1 further comprising glycerine, a water conditioning agent, one or more surfactants, or a mixture thereof.

5. The composition of claim 1 wherein the water-soluble polymer is a cationic hydroxypropyl guar or a cationic guar.

6. The composition of claim 1, wherein the suspending agent is selected from fumed silica, inorganic colloidal or colloid-forming particles, rheology modifier polymers, or mixtures thereof.

7. The composition of claim 1 wherein the water-soluble polymer is a water-soluble polysaccharide and wherein the hydration inhibitor component is present in an amount effective to inhibit hydration of the water-soluble polysaccharide in the aqueous medium and wherein the hydration inhibitor component further comprises at least one of: one or more surfactant compounds, one or more water-soluble non-surfactant salts, or one or more water dispersible organic solvents.

8. The composition of claim 1, further comprising a pesticide active ingredient, wherein the water-soluble polymer enhances delivery of the pesticide active ingredient from the liquid medium to a target substrate.

9. The composition of claim 1, wherein the liquid medium is an aqueous liquid medium that comprises water or water and a water immiscible organic liquid, and wherein the composition is in the form of an emulsion, a microemulsion, or a suspoemulsion.

10. The composition of claim 1, wherein:
the water-soluble polymer is selected from polyacrylamide polymers, non-derivatized guar polymers, derivatized guar polymers, and mixtures thereof, and
the suspending agent is selected from fumed silicas, inorganic colloidal or colloid-forming particles, rheology modifier polymers, water-soluble polysaccharide polymers other than the non-derivatized or derivatized guar polymer, and mixtures thereof.

11. The composition of claim 1 wherein the composition exhibits a viscosity of less than 10 Pa·s at a shear rate of greater than or equal to 10 $s^{-1}$.

12. The composition of claim 1 wherein the composition comprises, based on 100 parts by weight of the composition, greater than 2 parts by weight of an incompletely hydrated water-soluble polymer suspended in a liquid medium.

13. The composition of claim 1 wherein the composition comprises, based on 100 parts by weight of the composition, greater than 2.4 parts by weight of an incompletely hydrated water-soluble polymer suspended in a liquid medium.

14. The composition of claim 1 wherein the hydration inhibitor component further comprises choline bicarbonate, choline dihydrogen citrate, choline bitarate, potassium hydrogen phosphate, potassium carbonate, or any combination thereof.

15. The composition of claim 1 wherein the composition is free or substantially free of ammonium-containing compounds.

16. A concentrated adjuvant composition, comprising, based on 100 parts by weight of the composition,
from about 1 to about 20 parts by weight of an incompletely hydrated guar polymer suspended in aqueous medium, said guar polymer having a weight average molecular weight of from about 100,000 to about 5,000,000 grams per mole;
a hydration inhibitor component comprising a choline salt, dibasic potassium phosphate or a combination thereof; and
a suspending agent in an amount effective to impart shear thinning properties to the composition;
wherein said composition exhibits:
(a) a viscosity of greater than or equal to 5 Pa·s at a shear rate of less than 0.01 $s^{-1}$, and
(b) a viscosity of less than 5 Pa·s at a shear rate of greater than 10 $s^{-1}$.

17. The composition of claim 16 wherein the guar polymer comprises from about 2 parts to about 12 parts by weight based on 100 parts by weight of the composition.

18. The composition of claim 16 wherein the guar polymer comprises from about 2 parts to about 5 parts by weight based on 100 parts by weight of the composition.

19. The composition of claim 16 wherein the water-soluble polymer is a cationic hydroxypropyl guar or a cationic guar.

20. A method for making a concentrated adjuvant composition that comprises a mixture of an aqueous liquid medium, an incompletely hydrated water-soluble polymer dispersed in the aqueous liquid medium, and a hydration inhibitor component for inhibiting hydration of the water-soluble polymer, comprising:
contacting the hydration inhibitor component with the aqueous liquid medium, and
contacting the water-soluble polymer with the mixture of aqueous liquid and a hydration inhibitor component to disperse the water-soluble polymer,
wherein the hydration inhibitor component comprises choline chloride, dibasic potassium phosphate or a combination thereof.

21. The method of claim 20 further comprising contacting a suspending agent with at least one of the aqueous liquid medium, the water-soluble polymer, or the hydration inhibitor component.

22. The method of claim 20 wherein the water-soluble polymer is a cationic hydroxypropyl guar or a cationic guar.

23. The method of claim 20 further comprising contacting an agricultural pesticide compound to the composition.

* * * * *